US012400322B2

(12) United States Patent
Sloat et al.

(10) Patent No.: US 12,400,322 B2
(45) Date of Patent: Aug. 26, 2025

(54) SYSTEM AND METHOD FOR MEASURING EDEMA AT HOME AND MEASUREMENT PATTERN FOR USE THEREWITH

(71) Applicant: Fresenius Medical Care Holdings, Inc., Waltham, MA (US)

(72) Inventors: Daniel L. Sloat, Wakefield, MA (US); Lisa Sysun, Chelmsford, MA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 721 days.

(21) Appl. No.: 17/560,617

(22) Filed: Dec. 23, 2021

(65) Prior Publication Data

US 2022/0270241 A1   Aug. 25, 2022

Related U.S. Application Data

(60) Provisional application No. 63/151,952, filed on Feb. 22, 2021.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0013* (2013.01); *A61B 5/1077* (2013.01);
(Continued)

(58) Field of Classification Search
CPC ... A61B 5/1077; A61B 5/1079; A61B 5/4878; A61B 5/6898; A61B 5/7278; G01B 11/24
See application file for complete search history.

(56) References Cited

U.S. PATENT DOCUMENTS 5,178,146 A   1/1993   Giese
6,186,962 B1   2/2001   Lloyd et al.
(Continued)

FOREIGN PATENT DOCUMENTS

CN   204133473 U   2/2015
CN   104287892 B   12/2017
(Continued)

OTHER PUBLICATIONS

Extended European Search Report for EP Application No. 21927026.1, dated Nov. 13, 2024 (16 pages).
(Continued)

*Primary Examiner* — Eric F Winakur
(74) *Attorney, Agent, or Firm* — Kilyk & Bowersox, P.L.L.C.

(57) ABSTRACT

A system and method for measuring edema, at home, is provided, along with a measuring pattern for use therewith. The system includes a computing system that has an imaging device, a processor, a memory, and a wireless transmitter. The computing system is configured to capture edema data of a patient and send the data to a remote doctor. The pattern can be incorporated into a flexible sheet substrate that can be placed over a portion of a patient's skin. By pressing the flexible sheet substrate into the patient, a depression is formed and the pattern is distorted. The imaging device captures an image of the depression and the distorted pattern. The computing system processes the image and determines a depth of the depression based on the distortion of the pattern.

8 Claims, 9 Drawing Sheets

(51) Int. Cl.
    *A61B 5/107* (2006.01)
    *G06T 7/521* (2017.01)
    *G06T 7/70* (2017.01)
    *G16H 30/40* (2018.01)
    *G16H 40/67* (2018.01)

(52) U.S. Cl.
    CPC .......... *A61B 5/1079* (2013.01); *A61B 5/4878* (2013.01); *A61B 5/6898* (2013.01); *A61B 5/7278* (2013.01); *G06T 7/521* (2017.01); *G06T 7/70* (2017.01); *G16H 30/40* (2018.01); *G16H 40/67* (2018.01); *A61B 2562/164* (2013.01); *A61B 2576/00* (2013.01); *G06T 2207/10016* (2013.01); *G06T 2207/30088* (2013.01); *G06T 2207/30204* (2013.01)

(56) References Cited

U.S. PATENT DOCUMENTS

| | | | |
|---|---|---|---|
| 6,392,754 B1* | 5/2002 | Pingel | G01N 21/958 356/603 |
| 6,484,328 B1 | 11/2002 | Frazier | |
| 8,425,433 B2 | 4/2013 | Dunn et al. | |
| 9,317,913 B2 | 4/2016 | Carney | |
| 9,797,708 B2* | 10/2017 | Vredenborg | A61B 5/1079 |
| 9,855,009 B2* | 1/2018 | Segman | A61B 5/14552 |
| 9,996,925 B2 | 6/2018 | Pedersen et al. | |
| 10,219,739 B2 | 3/2019 | Mestha et al. | |
| 10,244,981 B2 | 4/2019 | Mir et al. | |
| 11,464,453 B2* | 10/2022 | Godavarty | A61B 5/14552 |
| 2006/0030791 A1 | 2/2006 | Billiar et al. | |
| 2007/0276309 A1 | 11/2007 | Xu et al. | |
| 2008/0077715 A1 | 3/2008 | Kochunni et al. | |
| 2008/0088855 A1* | 4/2008 | Maekawa | G01B 11/24 356/612 |
| 2010/0315422 A1* | 12/2010 | Andre | G01B 11/2513 345/426 |
| 2012/0238864 A1 | 9/2012 | Piferi et al. | |
| 2013/0245454 A1 | 9/2013 | Taskinen et al. | |
| 2014/0018779 A1 | 1/2014 | Worrell et al. | |
| 2015/0119721 A1 | 4/2015 | Pedersen et al. | |
| 2015/0150457 A1 | 6/2015 | Wu et al. | |
| 2017/0079575 A1 | 3/2017 | Darling | |
| 2017/0095208 A1 | 4/2017 | Oberleitner et al. | |
| 2018/0035970 A1 | 2/2018 | Avila | |
| 2018/0039734 A1 | 2/2018 | Jarlman et al. | |
| 2018/0360377 A1 | 12/2018 | Ulman et al. | |
| 2019/0029592 A1* | 1/2019 | Yao | A61B 5/443 |
| 2021/0259546 A1 | 8/2021 | Santos Garcia et al. | |

FOREIGN PATENT DOCUMENTS

| | | |
|---|---|---|
| JP | 2008-93158 A | 4/2008 |
| SU | 1491447 A1 | 7/1989 |
| WO | 2019136559 A1 | 7/2019 |
| WO | 2020005053 A1 | 1/2020 |

OTHER PUBLICATIONS

Chen et al., Camera-Based Peripheral Edema Measurement Using Machine Learning, 2018 IEEE, International Conference on Healthcare Informatics, pp. 115 et seq.

Wang et al., Smartphone-Based Wound Assessment System for Patients with Diabetes, IEEE Transactions on Biomedical Engineering, vol. 62, No. 2, Feb. 2015.

International Search Report for PCT Application No. PCT/US2021/065035, dated Apr. 18, 2022 (5 pages).

Written Opinion of the International Searching Authority for PCT Application No. PCT/US2021/065035, dated Apr. 18, 2022 (4 pages).

* cited by examiner

SYSTEM AND METHOD FOR MEASURING EDEMA AT HOME AND MEASUREMENT PATTERN FOR USE THEREWITH

CROSS-REFERENCE TO RELATED APPLICATION

The present application claims priority from U.S. Provisional Patent Application No. 63/151,952 filed Feb. 22, 2021, which is incorporated herein by reference in its entirety.

FIELD OF THE INVENTION

The present invention relates to measuring edema. The present invention also relates to remote monitoring of edema.

BACKGROUND OF THE INVENTION

Peripheral edema is a phenomenon in which there is an abnormal infiltration and excess accumulation of serous fluid in connective tissue and/or in a serous cavity in one or more of the body's extremities, such as feet, hands, ankles, calves, wrists, and arms. Peripheral edema can be benign and can correct itself in certain circumstances. It can also be, however, an indication of a variety of diseases, such as congestive heart failure (CHF), liver disease, kidney disease, lymphedema, hypoalbumenia, and chronic venous insufficiency. For example, in CHF, the presence of edema in the extremities (e.g., in the lower extremities) can be a valuable diagnostic marker for the presence of disease. In addition, the progression of the edemic state can be monitored over time and related to the progression of the disease.

The most widely used clinical method for assessing edema is digital manipulation, also known as the "pitting" method. This assessment is accomplished by pressing into the patient's skin near a bony surface and qualitatively evaluating the degree of pitting. Pitting is the indentation in the swollen tissue that remains following removal of the pressure from the edematous area. Due to the altered tissue composition resulting from edema, there can be a putty-like consistency to the tissue, and the tissue can remain in the indented position for several seconds before returning to its original form. The individual performing the test (doctor or other health care provider) assesses one or more of the depth of the indentation, how much force is required to reach a nearby bone, how long the tissue takes to return to its original state, and skin quality. The level of edema is typically described using a ranking system of one to three, corresponding to slight, moderate, and severe edema.

There is a need for additional methods of measuring edema that are reliable, economical, fast, easy to use, that provide repeatable measurements (from day to day and/or from practitioner to practitioner), and that have the potential to be used at home as well as in doctor's offices, hospitals, clinics, and veterinary settings.

SUMMARY OF THE INVENTION

A feature of the present invention is to provide reliable at home diagnostics for patients with edema.

Another feature of the present invention is to provide edema data of a patient to remote doctors, care partners, clinicians, and other caregivers.

A further feature of the present invention is to provide a pattern, an imaging device, and a computing system that enable remote doctors or other remote caregivers to gather edema data about a patient and that facilitate at home diagnostics of the patient.

To achieve these and other advantages, and in accordance with the purposes of the present invention, as embodied and broadly described herein, the present invention includes a system for measuring and monitoring edema. The system can include a flexible sheet substrate having a pattern. The flexible sheet can be configured to be placed on a surface of skin of a patient. The system can further include an imaging device and a computing system. The imaging device is configured to capture image data including an image of the pattern while the flexible sheet substrate is on the surface of the skin of the patient. The computing system includes a processor and a memory. The memory stores computer-readable instructions that, upon execution by the processor, configure the computing system to process image data captured by the imaging device. The image data includes at least an image of the pattern at a location on the surface of the skin of the patient, and a depression into the patient at the location. Processing the image data includes measuring a distortion of the pattern caused by the depression to determine a depth of the depression into the patient. The system can include a remote computing system. The computing system can further include a wireless transmitter configured to wirelessly transmit processed and/or unprocessed image data to the remote computing system. The remote computing system can be at a doctor's office.

According to one or more embodiments, an edema measuring sheet is provided. The edema measuring sheet can include a top flexible layer of a stretchable material, the top flexible layer having an upper surface and a lower surface and including a pattern that is visible when viewing the upper surface. An adhesive layer can be adhered to the lower surface of the top flexible layer and can be configured to be removably adhered to the skin of a patient. The pattern includes a series of parallel lines, for example, at least four parallel lines, and a grid comprising a plurality of markers that surrounds the series of parallel lines. When the edema measuring sheet is adhered to a location on the skin of the patient, and the location on the skin is depressed to form a depression into the patient, the edema measuring sheet is configured to stretch into and contour with the depression so that the pattern is distorted.

The present invention also relates to methods for measuring and monitoring edema. The measuring method can include the steps of: placing a pattern against a surface of skin of a patient, at a location; depressing a portion of the skin of the patient at the location of the pattern to cause a depression into the patient; and measuring a distortion of the pattern caused by the depression into the patient to determine a depth of the depression into the patient. The pattern can be part of a sheet of stretchable material. The placing of the pattern against the surface of the skin can comprise adhering a lower surface of the sheet to the surface of the skin at the location, such that the pattern is visible by viewing an upper surface of the sheet. The method can further include a step of capturing image data, with an imaging device. The image data can include an image of the pattern against the surface of the skin of the patient, and the depression at the location. The step of measuring the distortion of the pattern can include processing the image data. The method can further include wirelessly transmitting the image data, a grade or value based on the image data, or both, from the imaging device to a remote computing system, for example, over a wireless network. The remote computing system can be at a clinic, at a doctor's office, or the like.

It is to be understood that both the foregoing general description and the following detailed description are exemplary and explanatory only and intended to provide a further explanation of the present invention, as claimed.

BRIEF DESCRIPTION OF THE DRAWINGS

The invention may be more fully understood with reference to the accompanying drawings. The drawings are intended to illustrate, not limit, the present teachings, according to an embodiment of the present invention.

DETAILED DESCRIPTION OF THE INVENTION

Figure 1A:
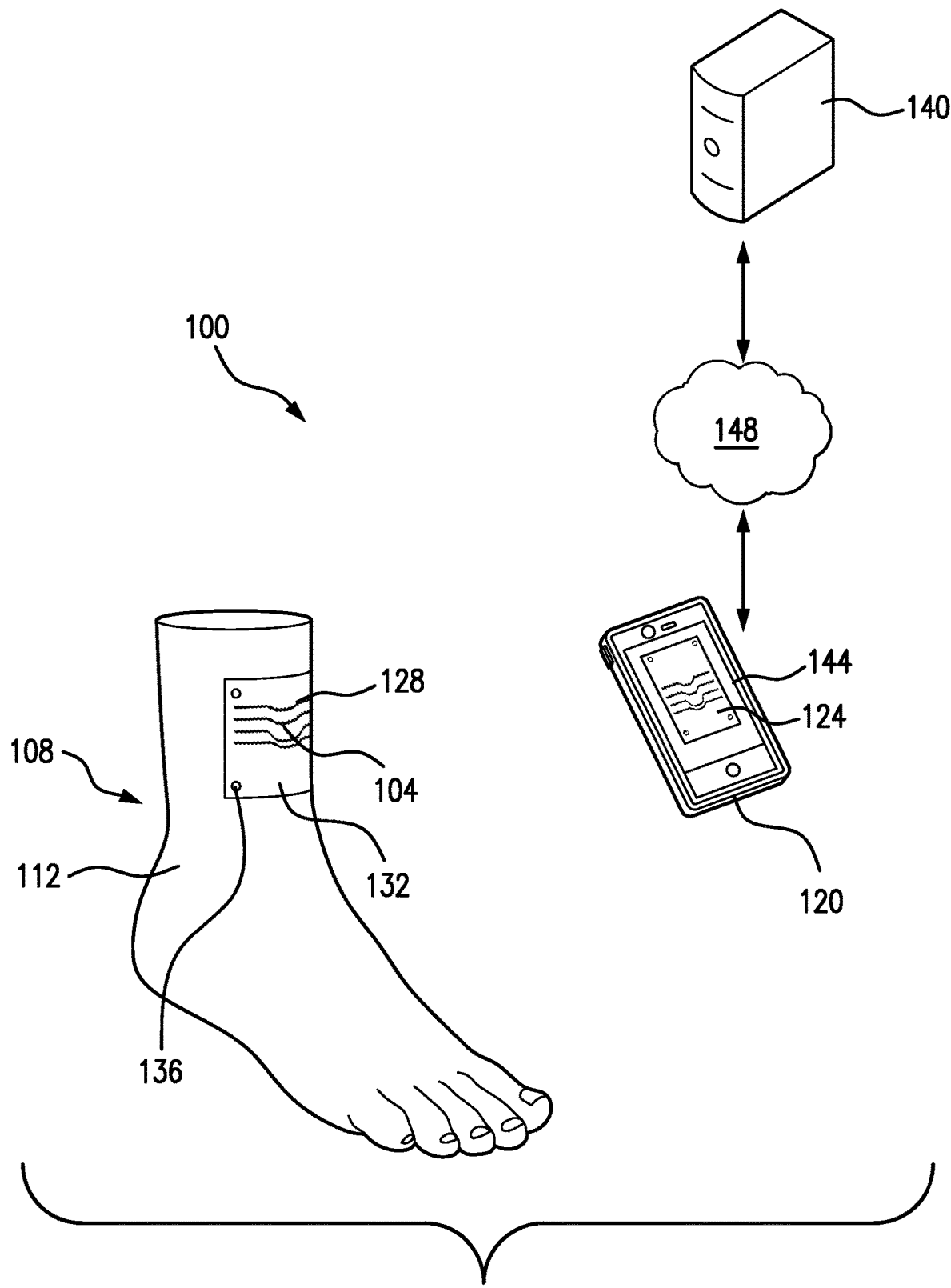
FIG. 1A is a schematic view of a flexible sheet substrate applied to a patient, an imaging device, a computing system, and a remote computing system, according to an embodiment of the present invention.

According to various embodiments, the present invention provides a system for measuring and monitoring edema. The system can comprise a flexible sheet substrate, an imaging device, and a computing system. The flexible sheet substrate can include a pattern and can be configured to be placed on the surface of the skin of a patient. The imaging device can be configured to capture image data including an image of the pattern while the flexible sheet substrate is on the surface of the skin of the patient. The computing system can comprise a processor and a memory. The memory can store a set of computer-readable instructions that, upon execution by the processor, can configure the computing system to process image data captured by the imaging device. The image data can comprise at least an image of the pattern at a location on the surface of the skin of the patient. The image data can also comprise a depression formed into the patient at the location. The depression can be formed by pressing a finger or probe against the skin of the patient, at the location, to form a depression, recess, indent, or other temporary abnormality in the skin. Processing the image data can comprise measuring a distortion of the pattern, caused by the depression, to determine a depth of the depression into the patient.

The flexible sheet substrate can comprise a stretchable material. The flexible sheet can have an upper surface and a lower surface, and the pattern can be visible from the upper surface. The lower surface can be configured to be adhered to the skin of the patient at the location. The flexible sheet substrate can comprise, for example, a top flexible layer comprising the upper surface of the flexible sheet. The top flexible layer can comprise a bottom surface. The flexible sheet substrate can comprise an adhesive layer having a first surface adhered to the bottom surface of the top flexible layer, and a second surface opposite the first surface, for example, an adhesive surface opposite the first surface. A removeable liner can be provided that is configured to be adhered to and protect the adhesive surface of the adhesive layer. The removable liner can be provided adhered to the adhesive surface so as to protect the adhesive surface. The removable liner can be peeled away from the adhesive surface, for example, just before use, such that and the adhesive surface is exposed.

The pattern on the flexible sheet substrate can comprise a series of parallel lines. The flexible sheet substrate can further comprise a plurality of markers surrounding the pattern, for example, in addition to the pattern and at corners of the pattern. The image data can further comprise an image of the plurality of markers. Upon execution of the computer-readable instructions by the processor, the computing system can be configured to determine an angle of the imaging device relative to the location on the surface of the skin, for example, by using the plurality of markers, relative positioning, angles, triangulation, and the like. The flexible sheet substrate can be of any shape. The flexible sheet substrate can comprise a plurality of corners and each of the plurality of markers can be disposed at a respective corner of the flexible sheet substrate.

The system can further comprise a remote computing system. The computing system can further comprise a wireless transmitter configured to wirelessly transmit image data to the remote computing system. The remote computing system can be located, for example, at a clinic, at a dialysis clinic, at a doctor's office, at a nurse's office, at a hospital, at a caregiver's location, or the like.

The system can further comprise a smart device. The smart device can comprise the imaging device and the computing system. The smart device can be, for example, a smart phone, a tablet, a smart watch, smart glasses, or the like. The smart device can be a smart phone that can comprise, for example, a touchscreen interface. The computer-readable instructions can be in the form of application software loaded on the memory, for example, an app loaded on a smart phone.

According to various embodiments, an edema measuring sheet is provided. The edema measuring sheet can comprise, for example, a top flexible layer and an adhesive layer, and can include a pattern as described herein. The top flexible layer can comprise, consist essentially of, or consist of, a stretchable material. The top flexible layer can have an upper surface and a lower surface and can include the pattern. The pattern can be visible when viewing the upper surface. In other words, if the imaging device focuses on the upper surface, the pattern can be imaged by the imaging device. The adhesive layer can be adhered to the lower surface of the top flexible layer. The adhesive layer can be configured to be removably adhered to the skin of a patient, for example, to be securely adhered to the skin but not to cause tearing, other injury, or a rash when removed from the skin. The pattern can comprise a series of parallel lines, for example, at least three, at least four, or more parallel lines. The pattern can include a grid, for example, comprising a plurality of markers that surrounds the series of parallel lines. The edema measuring sheet can be configured such that, when the edema measuring sheet is adhered to a location on the skin of a patient, and the location on the skin is depressed to form a depression into the patient, the edema measuring sheet can stretch into and contour with the depression so that the pattern is distorted. The amount or type of distortion can be analyzed to determine the extent of edema affecting the patient and to determine an appropriate course of action for treating the edema. The edema measuring sheet can further comprise a removable protective liner adhered to the adhesive layer.

The top flexible layer of the edema measuring sheet can comprise a plurality of markers. The top flexible layer of the edema measuring sheet can comprise a plurality of corners. The plurality of markers can include at least one respective marker disposed in each of the corners of the plurality of corners. The pattern can be printed on the upper surface of the top flexible layer. The pattern can be etched into the upper surface of the top flexible layer. The pattern can be embedded in the top flexible layer.

According to various embodiments, a container containing a plurality of edema measuring sheets is provided. The container can comprise an opening and a lid covering the opening. A plurality of edema measuring sheets as described herein can be disposed in the container. Each of the plurality of edema measuring sheets can include a removable liner protecting an adhesive surface of the respective edema measuring sheet.

A method for measuring edema is also provided according to the present invention. The method can involve placing a pattern against a surface of the skin of a patient, at a location, and depressing a portion of the skin of the patient at the location of the pattern. The depressing can be of sufficient force to cause the formation of a depression into the patient. The method can involve measuring a distortion of the pattern caused by the depression into the patient. The measuring can determine a depth of the depression into the patient. Based on the depth measured, determined, or calculated, an appropriate treatment for the patient can be figured out and prescribed.

The method can involve using a pattern that comprises a series of parallel lines. The pattern can be part of a sheet of stretchable material. The sheet can be configured to distort with and to be contoured to the depression into the patient. The method can involve a step of placing the pattern against the surface of the skin by adhering a lower surface of the sheet of stretchable material to the surface of the skin at the location. For example, the placement can result in the pattern being visible by viewing an upper surface of the sheet. The sheet of stretchable material can further comprise a plurality of markers surrounding the pattern. The sheet of stretchable material can comprise a plurality of corners and at least some of the plurality of markers can be disposed at respective corners of the plurality of corners. The method can involve capturing image data, with an imaging device, including an image of the pattern against the surface of the skin of the patient. The method can involve capturing image data, with an imaging device, including an image of the depression at the location. The step of measuring the distortion of the pattern can comprise processing the image data. The processing of the image data can be carried out by a computing system. The computing system and the imaging device can be parts of a smart device, for example, parts of the same smart device. The smart device can be selected from a smart phone, a tablet, a smart watch, smart glasses, and the like. The smart device can be a smart phone comprising a touchscreen interface.

The method can further comprise transmitting image data from the imaging device to a remote computing system, for example, over a wired or wireless network. A remote computing system can be at a doctor's office and the method can comprise wirelessly transmitting image data from the imaging device to a remote computing system at the doctor's office. In various embodiments, the image data can wirelessly-transmitted as a live stream video, to the remote computing system. By using the system, a smart device, and the method described herein, a patient can provide a doctor with important information that the doctor can use to assess edema in the patient, without the need for an office visit. The system and method can evaluate image data, provide a grade or score, for example, a one, a two, or a three, corresponding to whether the edema is slight, moderate, or severe. The system and method enable results, recommendations, and questions, to be discussed during a telehealth visit between the doctor and the patient, and over time can be used to monitor edema.

Other methods of placing a pattern on the skin of the patient can also, or instead, be used. For example, placing the pattern against the surface of the skin of the patient can comprise casting a light pattern against the surface of the skin of the patient. Placing the pattern against the surface of the skin of the patient can comprise transferring a temporary tattoo of the pattern against the surface of the skin of the patient. Placing the pattern against the surface of the skin of the patient can comprise forming a permanent tattoo of the pattern against the surface of the skin of the patient.

According to various embodiments, instead of an adhesive pad, a non-adhesive pattern sheet can be provided that can cling to a patient's ankle or other body part, via an electrostatic or similar charge. A method is provided that can comprise: (i) treating the non-adhesive pattern sheet to provide the non-adhesive pattern sheet with a non-neutral surface charge; and (ii) overlaying the non-adhesive pattern sheet on a patient's body part, for example, an ankle, such that the non-adhesive pattern sheet clings to the body part due to the non-neutral surface charge.

According to various embodiments, at least 20%, at least 30%, at least 40%, at least 50%, at least 60%, at least 70%, at least 80%, at least 90%, and/or at least 95% of the surface area of one side of the non-adhesive pattern sheet is in intimate clinging contact with the body part. Such surface-area percentages are considered herein to comprise a substantial portion of the cove non-adhesive pattern sheet. In some embodiments, about 25%, or about 50%, or about 75% of the surface area of one side of the non-adhesive pattern sheet can be caused to cling to the surface of the body part for a period of time (for example, for greater than 20 seconds).

The treating of the non-adhesive pattern sheet can comprise tribocharging (also known as "triboelectric charging," "contact charging" or "electrification by contact"). The treating can includes passing the non-adhesive pattern sheet through an electric field.

A charge differential can be established by triboelectric charging, inducing polarization, passage through an electric field, and the like. The charge differential can be at least 5V, at least 7V, at least 10V, at least 15V, at least 20V, at least 25V, at least 30V, at least 50V, at least 75V, at least 100V, or higher.

A plurality of non-adhesive pattern sheets can be provided. The plurality can comprise a laminar (multi-layer) sheet-like material having a first outer layer on one side and a second outer layer on an opposite side. The first and second layers can be comprised of first and second materials, with the first and second materials having unlike triboelectric properties. Accordingly, when surfaces of the first and second materials are brought into intimate contact with one another, and then separated, each acquires a non-neutral surface charge. The plurality of non-adhesive pattern sheets can be releasably connected to one another, end-to-end, and wound so as to define a roll configuration. The plurality of such sheet-like materials can be arranged in a stack, with each sheet-like material of the stack disposed in intimate contact with its nearest neighbors (or neighbor, in the case of the first and last sheets). The first layer of each sheet-like material of the stack can be disposed facing in a first direction and the second layer of each sheet-like material of the stack can be disposed facing in a second direction, wherein the second direction is opposite of the first direction. One of the layers can comprise, for example, of a paper material, for example, tissue, and the other of the layers can optionally be provided with adhesive properties, for example, a slight degree of stickiness or tackiness. At least one of the layers can comprise an electret.

A further aspect of the present invention provides a dispensing device for dispensing non-adhesive pattern sheets. The dispensing device can comprise: a compartment adapted to hold a plurality of non-adhesive pattern sheets; an orifice defined by a wall of the compartment permitting one of the non-adhesive pattern sheets to be pulled therethrough for removal from the compartment; and a charge-imparting member positioned such that a non-adhesive pattern sheet pulled through the orifice must pass closely by, for example, rub against, the charge-imparting member. In use, a non-adhesive pattern sheet removed from the dispenser via the orifice gains a non-neutral surface charge. The charge-imparting member and the non-adhesive pattern sheets can have unlike triboelectric properties. For example, non-adhesive pattern sheets can be made of a paper material and the charge-imparting member can comprise a vinyl or Styrofoam surface. The charge-imparting member can be an electrostatic generator.

According to various embodiments, the present invention exploits the phenomenon known as "triboelectric charging," or "tribocharging" for short. This phenomenon is also referred to as "contact charging" or "electrification by contact." There are several mechanisms that can contribute to the resulting charge that is generated by the triboelectric process. Four major factors that have the greatest influence on the triboelectric charging process are: surface contact effects; work function; charge back flow; and gas breakdown. These factors and other materials, systems, and methods that can be used in accordance with the present invention are described in U.S. Pat. No. 6,484,328 B1 to Frazier, which is incorporated herein in its entirety by reference.

In accordance with various embodiments of the present invention, a non-adhesive pattern sheet is tribocharged before it is finally placed on a patient's body part. The charge established on the non-adhesive pattern sheet provides a "cling" characteristic that assists in maintaining the non-adhesive pattern sheet in place once situated on the boy part. The affinity between the non-adhesive pattern sheet and the body part can be sufficient to maintain the non-adhesive pattern sheet in intimate clinging contact with the body part for at least 10 seconds, at least 15 seconds, at least 20 seconds, at least 30 seconds, at least 45 seconds, and/or at least one minute.

The non-adhesive pattern sheet can be incorporated into a square or rectangular sheet. Perforations or scoring can allow non-adhesive pattern sheets cover to be readily torn from the roll of such sheets. The non-adhesive pattern sheet is macroscopically two-dimensional and planar, although not necessarily flat. The non-adhesive pattern sheet has some thickness in the third dimension, but the third dimension is very small compared to the first two dimensions. The non-adhesive pattern sheet can exhibit good drapability. Drapability is the tendency of the non-adhesive pattern sheet to conform, normal to its plane, to a body part, such as a patient's ankle upon which the non-adhesive pattern sheet is placed. The higher the drapability of the non-adhesive pattern sheet, the more accurately it will conform to the body part. More accurate conformation to the body part can provide greater retention thereon. The non-adhesive pattern sheet can comprise a paper material, a soft tissue-type paper, a textile material, a cloth material, or the like. For a variety of reasons, in certain embodiments of the invention, fibrous non-adhesive pattern sheets, for example, comprising wood pulp, cellulosic, or paper-based materials, such as tissue-type paper, can generally be preferred. For example, such materials are most compatible with existing sewage and treatment facilities. Paper-based products are typically better in terms of biodegradability. A coating, for example, a water receptive wax, can be applied to form one or more layers on a paper sheet.

Tribocharging can be caused during unwinding of a non-adhesive pattern sheet from a roll. The non-adhesive pattern sheet can be provided as a roll, in the nature of a roll of paper towels or toilet paper, such that a user partially unwinds the roll to obtain the next-available non-adhesive pattern sheet which is then torn from the roll. Tearing can be aided by a perforation line or scoring. The non-adhesive pattern sheet can be a laminate article comprising upper and lower sides of different materials with a spaced-apart ranking in the triboelectric series. For example, one side of each non-adhesive pattern sheet can be a paper-based tissue-type material, and the other side can be a rubber-based film layer, so that tribocharging occurs upon unrolling in a fashion analogous to the tape-dispenser. A dispenser in the nature of an elongated rod can be utilized to receive a roll in a manner permitting unwinding of the roll thereabout.

So-called "cling films" can be used as the non-adhesive pattern sheet material. Nonlimiting examples of films include polyvinyl chloride films (whether plasticized or flexible), polyurethane films, high density polyethylene films, polypropylene films, tackified linear low density polyethylene films, acrylonitrile/butadiene/isoprene films, acrylonitrile/butadiene copolymers, styrene/butadiene copolymers (whether random or block), styrene/isoprene copolymers (whether random or block), styrene/ethylene-butylene block copolymers, and combinations thereof, as well as other films known in the art for making cling films. A "cling" property can be imparted to plastic film by including a high content of plasticizer in the plastic. Polyvinyl chloride films with this property are commercially available from several sources. An example of film having a cling property is Sure-State Series 9000, which is available from Tekra Corporation, New Berlin, Wisconsin. Permacharge Corp., Rio Rancho, N. Mex., provides an electrostatic polypropylene material called ClingZ. ClingZ gets its adhesive properties from a permanent electrostatic charge. The film is repositionable like other cling films, but ClingZ contains no plasticizers. The present invention contemplates the use of such material, as well, in the make-up of a non-adhesive pattern sheet herein. The non-adhesive pattern sheet can comprise an electrostatically charged nonwoven fabric.

Figure 1B:
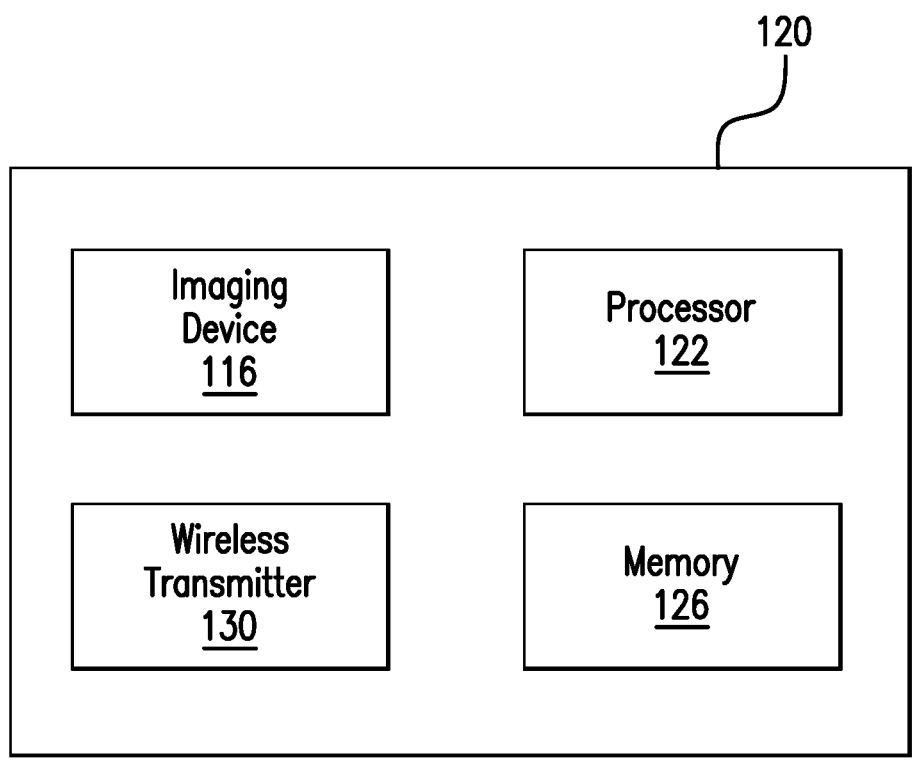
FIG. 1B is a block diagram of components of the computing system shown in FIG. 1A.

Referring to FIGS. 1A and 1B, FIG. 1A depicts a system for measuring and monitoring edema 100, according to an exemplary embodiment of the present invention. FIG. 1B depicts a block diagram of a computing system 120, according to an exemplary embodiment of the present invention. System 100 can include a flexible sheet substrate 132 having a pattern 104. System 100 includes an imaging device 116 and computing system 120. Computing system 120 can comprise imaging device 116, a processor 122, a memory 126, computer readable instructions stored in memory 126, and a wireless transmitter 130. A patient 108, a physician, a technician, a caregiver, a care partner, or another user can place flexible sheet substrate 132 on a surface of the skin 112 of the patient at the patient's foot, hand, ankle, calf, wrist, arm, or the like. The user then presses into the patient's skin 112 at a location overlaid by pattern 104 to cause a depression 128. Depression 128 can be formed by pressing a finger or probe against skin 112 of patient 108, at the location. If any sort of depression 128 remains in the patient after the pressure is released, the user captures an image of the depression and pattern, or, more generally, image data, using imaging device 116. Imaging device 116 can be a cell phone camera and computing system 120 can be a cell phone. The image data can be captured by the imaging device 116 within 1 second, within 2 seconds, within 3 seconds, within 4 seconds, within 5 seconds, within 6 seconds, within 8 seconds, within 10 seconds, within 15 seconds, or longer, after the pressure is released. The image data includes an image 124 of pattern 104 on the surface of skin 112 of patient 108, and depression 128 into patient 108 at the location of pattern 104. Computing system 120 then processes the image data by measuring a distortion of pattern 104 caused by depression 128 to determine a depth of depression 128 into patient 108.

Computing system 120 can be a smart device, laptop, desktop, server, or the like. Examples of smart devices can include a smart phone, a tablet, a smart watch, and smart glasses. As illustrated in FIG. 1A, computing system 120 can include a smart phone that has a touch screen interface 144. The smart phone can comprise computing system 120, including imaging device 116. In such embodiments, the computer-readable instructions are in the form of application software (app) loaded in the memory of the smart phone. After depression 128 is made, the user can capture an image 124 of the depression using imaging device 116 and touch screen interface 124 of the smart phone.

Although pattern 104 is illustrated as being part of flexible sheet substrate 132, pattern 104 can be provided via a different medium. For example, pattern 104 can be drawn on the patient using a marker, pattern 104 can be projected onto skin 112 by a light projector, pattern 104 can be part of a permanent or temporary tattoo, or the like. Pattern 104 can include a series of parallel lines each disposed in a horizontal direction and located above and below one another. Pattern 104 can include a series of parallel lines each disposed in a vertical direction and located side by side. Pattern 104 can include a series of parallel lines disposed in diagonal directions. Pattern 104 can include a grid pattern including a plurality of vertical and horizontal lines crisscrossing one another. Pattern 104 can include a series of dots, a series of wavy lines, a series of zigzags, or any pattern that can be preloaded on memory 126 and recognized by computing system 120. If a series of parallel lines, the pattern can comprise, for example, at least three, at least four, at least five, at least six, or more parallel lines.

Flexible sheet substrate 132 can further include a plurality of markers 136 surrounding pattern 104, for example, a quick response (QR) code. Plurality of markers 136 can comprise markers in each corner of the flexible sheet substrate, in three of four corners of the flexible sheet substrate, in an arc partially surrounding the pattern, in a circle surrounding the pattern, or the like. Each marker of plurality of markers 136 can independently be any shape, such as a circle shape, a square shape, a rectangular shape, a triangular shape, a trapezoid shape, a star shape, or another shape. As illustrated in FIG. 1A, markers 136 can include circle shapes disposed at each of the corners of flexible sheet substrate 132. The plurality of markers 136 allows computing system 120 to perform geometric calculations to determine where, and at what angle, imaging device 116 is situated relative to pattern 104.

When computing system 120 and imaging device 116 are part of a smart device, the app can guide the user to capture the image. For example, the smart device can include a display. The app can guide the user and prompt the user to capture an image that can be readable by computing system 120 by displaying brackets, a rectangle, a square, lines, dots, or other imaging guides on the display that overlay a live feed from imaging device 116. The app prompts the user to capture the image when pattern 104 is within the imaging guide during the live feed of the imaging device 116. This ensures that computing system 120 is capable of processing the captured image to determine the depth of depression 128. The app can also provide a timer for computing system 120 to measure a period of time. For example, when pressure is released from skin 112, timer can be activated by the user pressing an activator on touchscreen interface 144. Timer can automatically stop when the image is captured by the user. An amount of time between when pressure is released and when the image is captured, can be recorded. The amount of time can be superimposed on the image or can be incorporated with the image data in other fashions. The length of time between when pressure is released and when the image is captured, can be used to adjust, calibrate, or modify the image data or the image data and processor can otherwise calculate a score of the depression based, in-part, on the length of time. If the length of time between when pressure is released and when the image is captured, is too long, an error message or signal can be sent or generated or both.

As mentioned above, computing system 120 processes the image data by measuring a distortion of pattern 104 caused by depression 128, and using the distortion, determines a depth of depression 128 into patient 108. Computing system 120 can first perform geometric calculations to determine an angle of imaging device 116 relative to skin 112 of patient 108 at the location of pattern 104, and the geometric calculations can be made by using plurality of markers 136. A distance between markers 136 can be preloaded on memory 126 of computing system 120.

Computing system 120 can determine the angle by calculating the difference between the distance of markers 136 in the image compared with the actual distance between markers 136 on the flexible sheet substrate 132 and then calculating the relative angle. Once the angle is determined, computing system 120 can use the angle and the distortion of pattern 104 to determine a depth of depression 128 into patient 108. Pattern 104 can be preloaded on the memory of computing system 120. Computing system 120 can compare pattern 104 on the image with a preloaded version of pattern 104 to determine an extent of distortion in pattern 104 and to thereby determine a depth of depression 128. The depth of depression 128 can be displayed on a display of computing system 120, a display of a remote computing system 140, on both, or not at all.

Once the depth of depression 128 is determined, computing system 120 can assign a severity level of depression 128 and display the severity level to the user, a remote doctor, a caregiver, a care partner, or the like. For example, the levels can be based on a scale such as a three-point scale or a four-point scale. An exemplary four-point scale can include a slightly pitted level 1, a somewhat pitted level 2, a deeply pitted level 3, and a severely deeply pitted level 4. Computing system 120 can thereby determine the severity of depression 128 and can display the severity to the user, remote doctor, caregiver, care partner, or the like. Other types of grading scales can be used and presented on a display.

Computing system 120 can further include a wireless transmitter 130 that wirelessly transmits data over a wireless network 148. For example, computing system 120 can send data to remote computing system 140 or remote servers over the Internet. Image data can be processed on computing system 120, at remote computing system 140, or both. Processed and unprocessed image data, as well as severity levels, can be saved on the memory of computing system 120, on a memory of remote computing system 140, on a remote server such as a cloud-based server, or on a combination thereof.

Determining the depth of depression 128 can be performed on computing system 120 that is hard wired to imaging device 116, on a remote computing system 140, or both. For example, the user can capture the image data and the depth can be calculated on the app of the smart device. Once the depth of depression 128 is calculated, depth data including the depth of depression 128, severity level, or both, can be sent to remote computing system 140 over wireless network 148. In certain embodiments, the user can capture the image data and then the image data is sent to remote computing system 140 over wireless network 148 for remote computing system 140 to determine the depth of the depression 128, the severity level, or both.

Additionally, image data, depth data, or both can be combined with other diagnostic data to be sent to remote computing system 140. Other diagnostic devices that capture diagnostic data of the patient can communicate with computing system 120 via BLUETOOTH, WIFI, or other wired or wireless connections, to combine the diagnostic data with the image data, depth data, severity level, or a combination thereof. For example, heart rate, blood pressure, video screenings, audio screenings, or other diagnostic data of the patient can be captured by one or more diagnostic devices and can be sent over a wire or wirelessly to computing system 120 or to a central computing hub. The diagnostic data can be combined with the image data, depth data, severity level, or a combination thereof as a data package and the data package can be sent to remote computing system 140 for a remote doctor, or the like, to review.

Remote computing system 140 can be at a clinic, at a dialysis clinic, at a doctor's office, at a nurse's office, at a hospital, at a caregiver's location, at a veterinary's office, or the like. System 100 of the present invention allows a remote patient to send diagnostic data, image data, depth data, severity level, or a combination thereof to remote computing system 140 of a remote doctor such that the remote doctor can diagnose the patient remotely. Thus, the present invention can be used to prevent exposure of patients to environments conducive to contracting diseases, such as COVID-19, or other viral and bacterial infections. Once the remote doctor has received diagnostic data, image data, depth data, severity level, or a combination thereof, and the depth of depression 128 is determined, the remote doctor can determine an extent of edema of the patient and prescribe appropriate treatments. Additionally, each of the diagnostic data, image data, depth data, severity level, or a combination thereof can be stored on a memory of either computing system 124, remote computing system 140, or a remote server. Depths of multiple depressions, captured over time, can be saved and compared. Images over time can be processed to provide a time lapse, or the like, to determine if a patient's health is improving or deteriorating.

Figure 2:
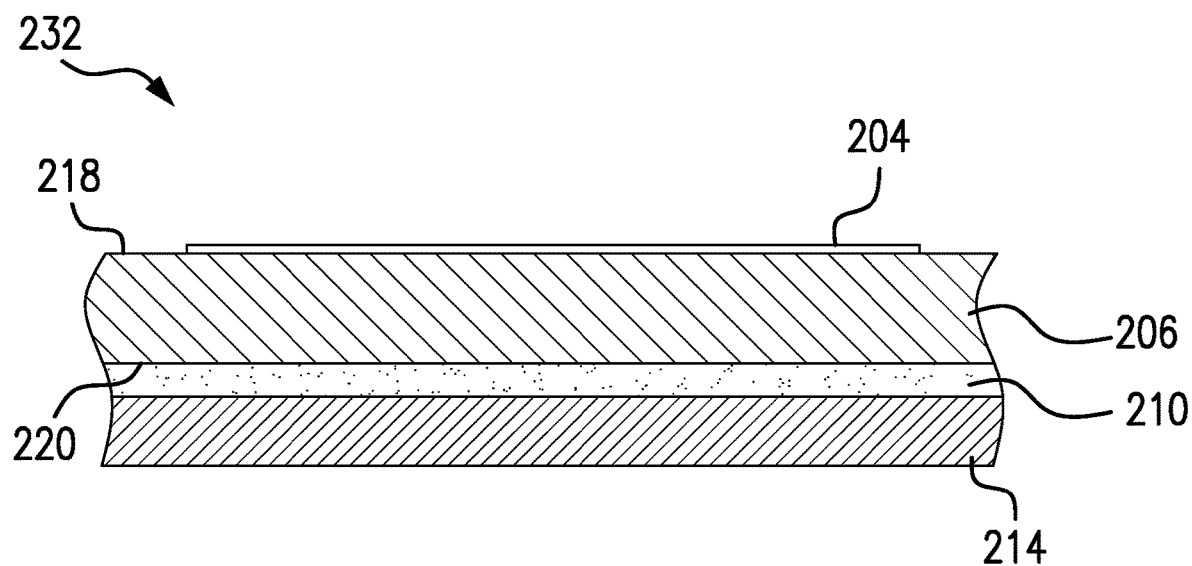
FIG. 2 is a cross-sectional view of a flexible sheet substrate, according to an embodiment of the present invention.

FIG. 2 illustrates a cross sectional view an edema measuring sheet that includes flexible sheet substrate 232. Flexible sheet substrate 232 can include a top flexible layer 206 and a pattern layer or pattern 204. Top flexible layer 206 can be placed against the skin of a patient such that pattern 204 is covering a portion of the skin. Top flexible layer 206 can be attached to the skin by an adhesive, by electrostatic forces, by tribocharged forces, by being held by a user, or the like.

Flexible sheet substrate 232 can have a width and a length, each independently of from 1 inch to 10 inches, from 2 inches to 8 inches, from 4 inches to 6 inches, or of 5 inches. Flexible sheet substrate 232 can have a thickness of from 6 μm to 6 mm, from 10 μm to 2 mm, from 20 μm to 1 mm, or from 50 μm to 0.5 mm. Flexible sheet substrate 232 can be of any shape, such as a square shape, a rectangular shape, a circular shape, an oval shape, a trapezoid shape, or the like, and can have a flat profile made of a flexible and stretchable material. For example, flexible sheet substrate 232 can have rectangular shape with four corners. Flexible sheet substrate 232 can be capable of stretching from 10% up to 50%, from 15% up to 45%, from 20% up to 40%, from 25% up to 35%, or 30% beyond its resting length, resting width, or both. Top flexible layer 206 can be made of a stretchable material such as, but not limited to, a flexible fabric, a flexible polymer, or a combination thereof. The flexible polymer can include a thin sheet of polyethylene, polypropylene, ethylene vinyl acetate (EVA), polyurethane, and the like.

Top flexible layer 206 can have an upper surface 218 and a bottom surface 220. Top flexible layer 206 further includes pattern 204 that is visible when viewing upper surface 218. As illustrated in FIG. 2, pattern 204 is printed on or attached to upper surface 218 of top flexible layer 206. Alternatively, pattern 204 can be etched on the upper surface of top flexible layer 206, embedded inside of top flexible layer 206, screen printed on top flexible layer 206, laser printed on top flexible layer 206, or the like.

Top flexible layer 206 can include any color that contrasts with a color of pattern 204 such that pattern 204 is easily visible. For example, top flexible layer 206 can be white, while pattern 204 can be black, or vice versa. In certain embodiments, top flexible layer 206 can be opaque and pattern 204 can include a dark color that is easily visible when applied to the skin of the patient.

Flexible sheet substrate 232 can further include an adhesive layer 210. Adhesive layer 210 can include a first surface adhered to bottom surface 220 of top flexible layer 206.

Adhesive layer 210 can also have an adhesive surface opposite the first surface. The adhesive that forms adhesive layer 210 can be sufficiently flexible to follow the skin, can be irritant-free to the skin, can be free of chemicals that would cause chemical stimulation, can be free of properties that would cause physical stimulation, and can have moisture permeability. For example, the adhesive can be selected form synthetic rubber adhesives, styrene-isobutylene-styrene copolymer adhesives, polyurethane adhesives, polysiloxane adhesives, natural rubber adhesives, polyether adhesives, acrylic adhesives, wax adhesives, or a combination thereof. The adhesive can contain various additives, if desired, for example, plasticizers represented by polyvalent alcohols such as glycerol, polyethylene glycol, polypropylene glycol, and the like, aqueous or water-absorbable resins such as polyacrylic acid, crosslinked polyacrylic acid, polyvinylpyrrolidone, and the like, rosin, terpene, petroleum tackifiers, softeners, fillers, pigments, thickeners, and the like. Adhesive layer 210 is removably adhered to the skin of a patient, for example, to be securely adhered to the skin but not to cause tearing, other injury, or a rash when removed from the skin. For example, the adhesive strength can be 10 g/inch to 200 g/inch, 30 g/inch to 150 g/inch, 40 g/inch to 100 g/inch, 50 g/inch to 70 g/inch, or 60 g/inch.

A removable protective liner 214 can adhere to the lower adhesive surface of adhesive layer 210 and can cover adhesive layer 210. Removeable liner 214 can protect adhesive layer 210 from debris and moisture and can preserve the adhesiveness of adhesive layer 210. Removeable liner 214 can be peeled away from the lower adhesive surface such that the adhesive surface is exposed so that the edema measuring sheet can be adhered to the skin of the patient when ready for use.

Figure 3:
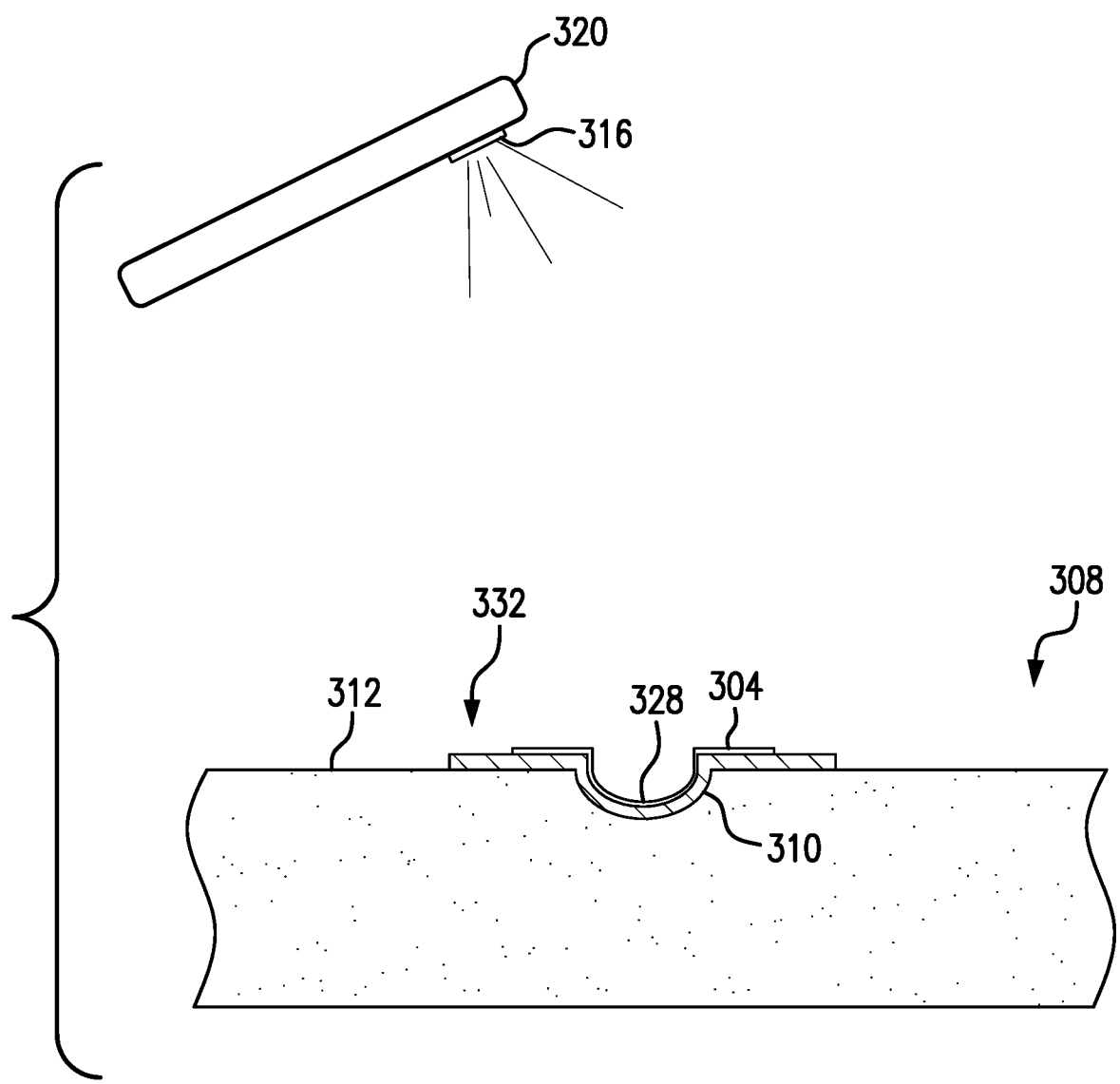
FIG. 3 is a partial cross-sectional view of a flexible sheet substrate applied to a patient, and a side view of a computing system including an imaging device positioned to image the flexible sheet, according to an embodiment of the present invention.

FIG. 3 is a cross-sectional view of a flexible sheet substrate 332 wherein a removeable liner has been peeled away from an adhesive layer 310 and adhesive layer 310 has been adhered to a patient's skin 312. As illustrated in FIG. 3, a depression 328 is formed in patient 308 and a pattern 304 has been distorted. An imaging device 316 of a computing system 320 captures image data of depression 328 and computing system 320 is configured to determine a depth of depression 328 based on the distortion of pattern 304.

Figure 4:
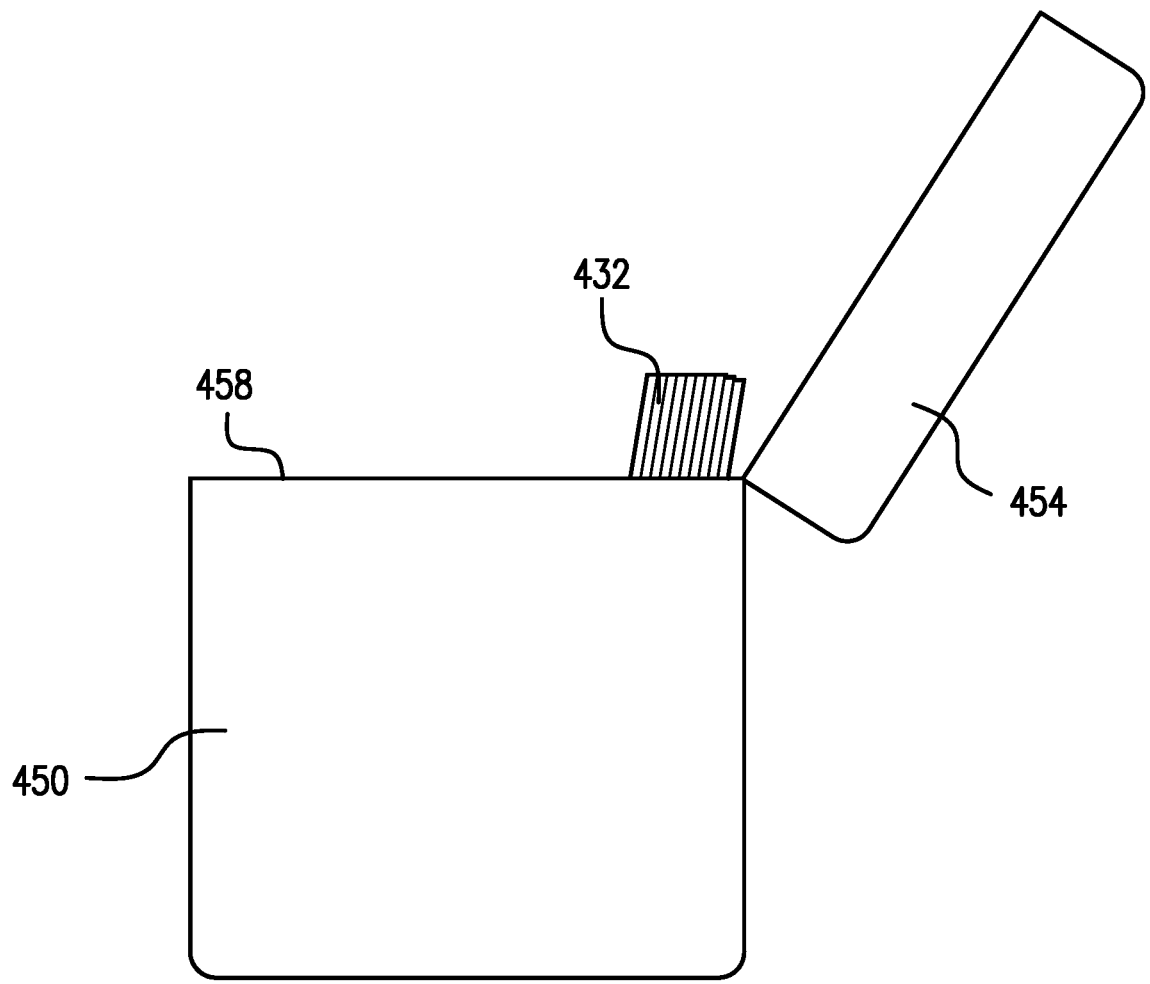
FIG. 4 is a side view of a container and a plurality of flexible sheet substrates disposed in the container, according to an embodiment of the present invention.

FIG. 4 illustrates a container 450 containing a plurality of edema measuring sheets 432. Container 450 can include an opening 458 and a lid 454 that can cover the opening or be hinged-back to enable access to edema measuring sheets 432. Lid 454 can be connected to container 450 by a hinge, a friction fit, clasps, locks, ties, magnets, or the like. A plurality of edema measuring sheets 432, as described herein, can be disposed in container 450. Each of the plurality of edema measuring sheets 432 can include a removable liner protecting an adhesive surface of the respective edema measuring sheet 432. Alternatively, edema measuring sheets 432 can be stored in container 450 in the form of a roll. Lid 454 can be opened, exposing edema measuring sheets 432 such that at least one edema measuring sheet 432 can be removed and used. Edema measuring sheet 432 can be a disposable item or can be reusable and placed back into container 450. After removing an edema measuring sheet 432, lid 454 can be closed and container 450 can be stored. Edema measuring sheets 432 can be packaged and shipped in container 450. Additionally, container 450 can be used for storage of edema measuring sheets 432 at a home of a patient, at a doctor's office, at a clinic, at a hospital, at a veterinary office, or the like.

Figure 5:
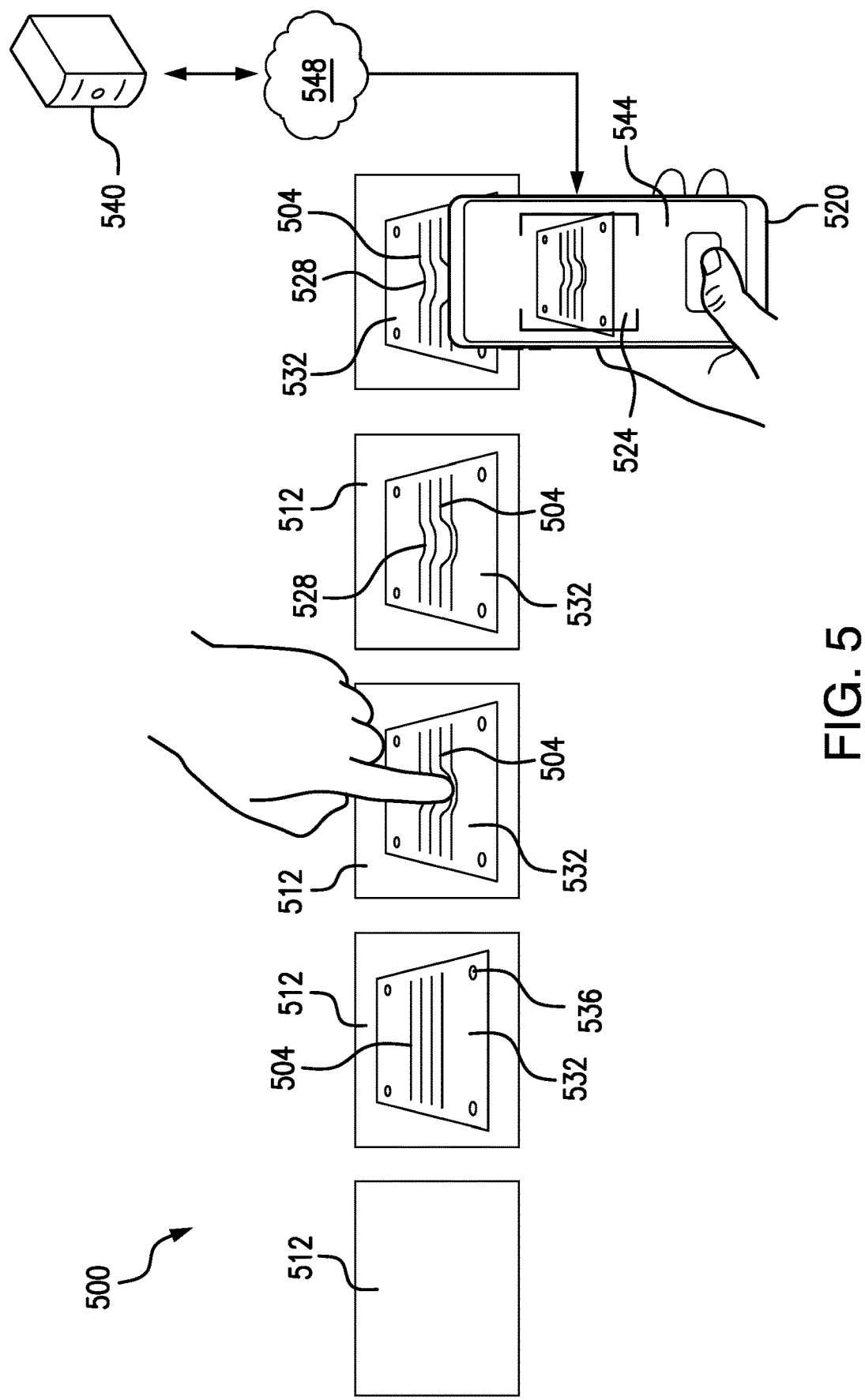
FIG. 5 is a schematic view illustrating each of a plurality of steps of a method, according to an embodiment of the present invention.

FIG. 5 illustrates a method for measuring edema, which involves a number of steps 500. Steps 500 can involve placing a pattern 504 against a surface of a skin 512 of a patient, at a location, and depressing a portion of the skin of the patient at the location of pattern 504. The depressing can be of sufficient force to cause the formation of a depression 528 into the patient. Steps 500 can involve measuring a distortion of pattern 504, caused by depression 528 into the patient. The measuring can determine a depth of depression 528 into the patient. Based on the depth measured, determined, or calculated, an appropriate treatment for the patient can be figured out and prescribed. Over time, the edema can be monitored.

Pattern 504 includes a series of parallel lines or another pattern 504 as described herein. Pattern 504 can be part of a sheet 532 of stretchable material, can be a light projection, can be drawn onto skin 512 by a marker, can be part of a temporary or permanent tattoo, or the like. Sheet 532 can be configured to distort with and to be contoured into depression 528 in the patient. Steps 500 can involve a step of placing pattern 504 against the surface of the skin by adhering a lower surface of sheet 532 of stretchable material to the surface of skin 512 at the location. Alternatively, sheet 532 can attach to skin 512 by electrostatic forces or can be held against skin 512 by a user. The placement can result in pattern 504 being visible by viewing an upper surface of sheet 532. Sheet 532 of stretchable material can further include a plurality of markers 536 surrounding pattern 504. Sheet 532 of stretchable material can include a plurality of corners and at least some of the plurality of markers 536 can be disposed at respective corners of the plurality of corners. Method 500 can involve capturing image data, with an imaging device, including an image 524 of pattern 504 against the surface of skin 512 of the patient. Steps 500 can involve capturing image data, with an imaging device, including an image 524 of depression 528 at the location. The step of measuring the distortion of pattern 504 can include processing the image data. The processing of the image data can be carried out by a computing system 520. Computing system 520 and imaging device can be part of a smart device, for example, part of the same smart device. The smart device can be selected from a smart phone, a tablet, a smart watch, smart glasses, and the like. The smart device can be a smart phone having a touchscreen interface 544.

Steps 500 can further include transmitting image data from the imaging device to a remote computing system 540, for example, over a wired or wireless network 548. Remote computing system 540 can be at a doctor's office and steps 500 can include wirelessly transmitting image data from the imaging device to remote computing system 540 at the doctor's office. In various embodiments, the image data can be wirelessly-transmitted as a live stream video, to remote computing system 540. Method 500 can further include storing image data, depth data, a severity level score, or a combination thereof, to a memory of either computing system 520, remote computing system 540, or a remote server. The depths of multiple depressions can be compared. Images 524 can be further processed by computing system 520 and/or remote computing system 540. A time-lapse sequence, series, video, or the like, can be generated to determine if a patient's health is improving or deteriorating over time. The method comprising steps 500 enables a patient to provide a doctor with important information that the doctor can use to assess edema in the patient, without the need for an office visit. The method enables results, recommendations, and questions, to be discussed during a telehealth visit between the doctor and the patient.

Figure 6:
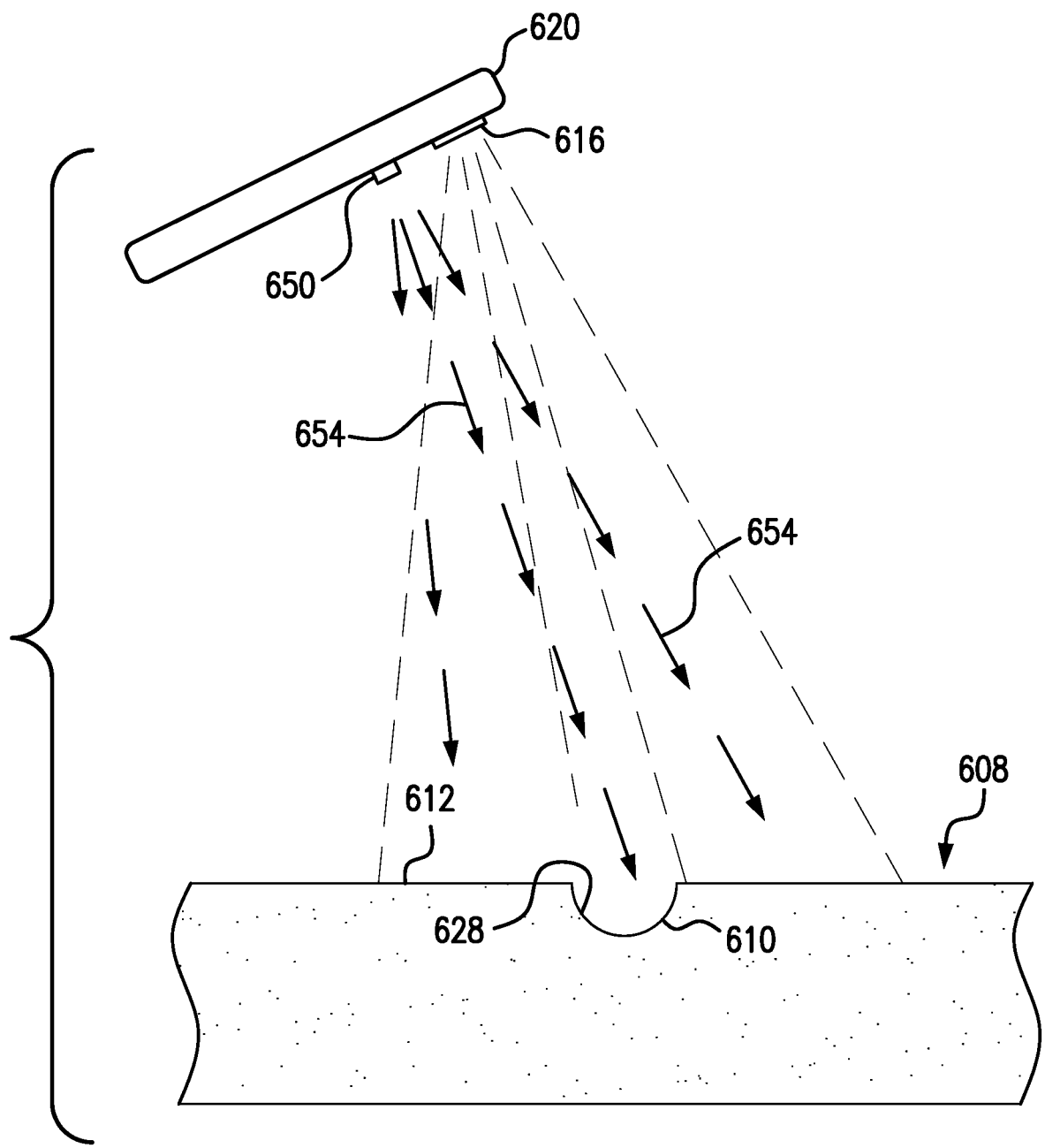
FIG. 6 is a cross-sectional view of a patient's ankle having a depression formed therein, and a side view of a combined pattern-casting and imaging device casting a pattern on the ankle and imaging the pattern.

FIG. 6 is a side view of an exemplary embodiment in which a pattern is projected onto skin 612 of a patient 608 in the form of light, without the need for a flexible sheet. The light pattern can be projected onto the skin by a pattern projector 650 that can project any type of visible light, such as laser light. A computing device 620, including imaging device 616 and pattern projector 650, can all be part of the same smart device or parts of devices that are separate from one another. In certain embodiments, pattern projector 650 can be separate from the smart device and removably attached thereto. For example, pattern projector 650 can be part of an adapter that is removably attached to the smart device by clips, adhesives, magnets, ties, mating slots, or the like. Pattern projector 650 can include a fitting and can be configured to fit over a flashlight feature of a cell phone device.

As shown in FIG. 6, a depression 628 is made into patient 608 by pressing against skin 612. Pattern projector 650 projects light 654 in the form of the pattern, onto depression 628. The light pattern is distorted due to depression 628. Imaging device 616 captures an image of the distorted light pattern and depression 628. Computing system 620 compares a preloaded pattern to the distorted light pattern that has been captured and calculates the depth of depression 628.

Figure 7:
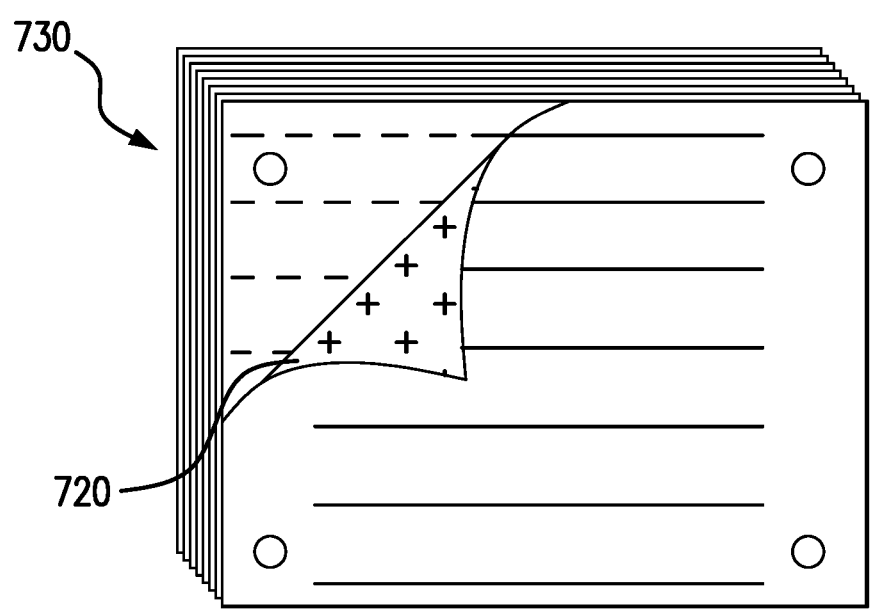
FIG. 7 is a partially schematic, perspective view illustrating triboelectric charging upon peeling a non-adhesive pattern sheet from a stack, where each non-adhesive pattern sheet has front and back surfaces of first and second respective materials having disparate triboelectric properties.

FIG. 7 is a partially schematic illustration of an embodiment of the present invention wherein a plurality of non-adhesive pattern sheets is arranged in a stack, denoted generally as 730. Each non-adhesive pattern sheet of the stack is disposed in intimate contact with its nearest neighbors (or neighbor, in the case of the first and last sheets). A biasing mechanism can be provided to keep the non-adhesive pattern sheets in pressing engagement. Each non-adhesive pattern sheet is comprised of at least two layers. The two layers are comprised of materials differing from one another with respect to their triboelectric properties. A first outermost layer of each non-adhesive pattern sheet of the stack is disposed facing in a forward direction and an outermost layer on the opposite side of each non-adhesive pattern sheet is disposed facing in a reverse direction. Triboelectric charging is caused by peeling a non-adhesive pattern sheet 720 from stack 730. Attention is directed to the plus (+) and minus (−) signs in FIG. 7, indicating positive and negative surface charges upon peeling. Conveniently, the non-adhesive pattern sheets of the present invention can be provided for use with a dispenser, for example, a dispenser configured to hold, for example, 50 or 100 non-adhesive pattern sheets.

Figure 8:
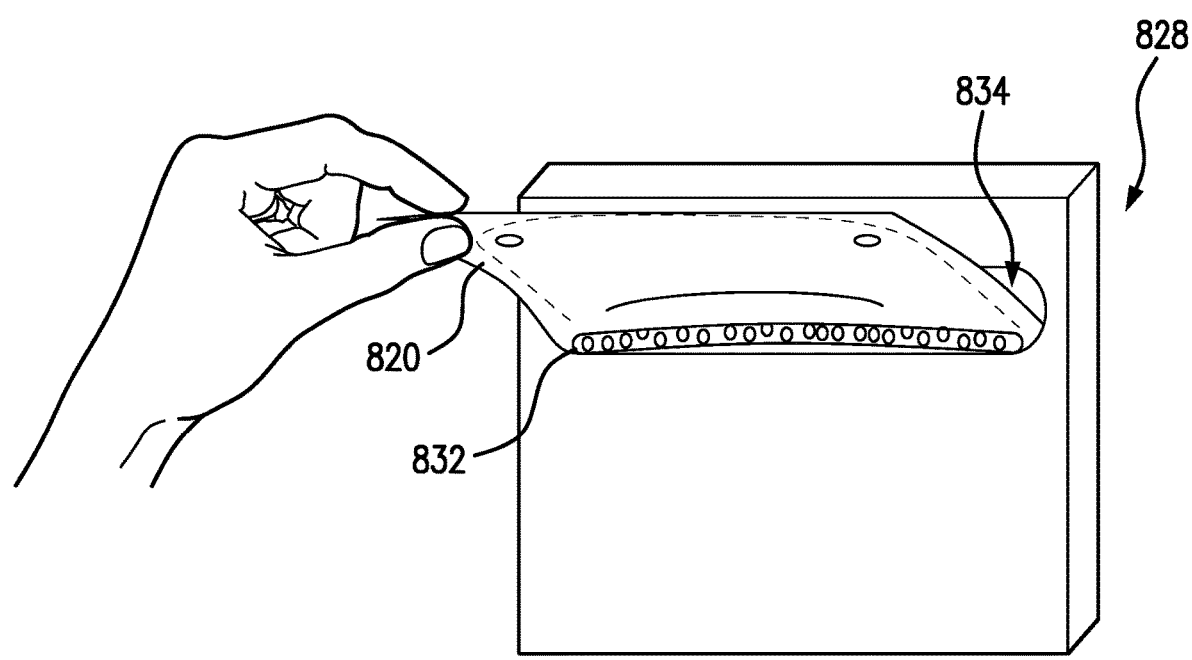
FIG. 8 is a perspective view of a dispenser for non-adhesive pattern sheets, having a charge-imparting member mounted near an orifice through which individual non-adhesive pattern sheets can be drawn and charged, according to an embodiment of the present invention.

FIG. 8 illustrates a dispenser 828 for non-adhesive pattern sheets, having a charge-imparting member 832 mounted near an orifice 834 through which individual non-adhesive pattern sheets, such as sheets 820, can be pulled. Charge-imparting member 832 can comprise a vinyl or Styrofoam member mounted at an orifice of dispenser 828, through which orifice fresh non-adhesive pattern sheets are pulled. For example, a vinyl member can include a surface portion disposed such that a non-adhesive pattern sheet pulled through the orifice is forced to contact it, thereby providing a means for contact electrification. The vinyl member can be bonded to the body of dispenser 828 by means of a suitable insulating adhesive that will not adversely affect its electrostatic properties. An electrostatic generator can be mounted on the dispenser such that it imparts a persistent electrostatic charge to a cover as the cover is removed from the dispenser.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for measuring edema, comprising:
   depressing a portion of skin of a patient at a location, by pressing a finger against skin of the patient, at the location, to apply pressure with the finger and cause a depression into the portion of the skin of the patient;
   releasing the pressure applied with the finger;
   casting a light pattern against the surface of the skin of the patient, including the depression, at the location, after the pressure is released, the light pattern being cast from a combined pattern-casting and imaging device and being distorted due to the depression;
   capturing an image of the distorted light pattern, with the combined pattern-casting and imaging device, within 15 seconds after the pressure is released;
   using a computing system to compare the image of the distorted light pattern with a preloaded pattern, to form a comparison; and
   using the computer system to calculate a depth of the depression, based on the comparison.

2. The method of claim 1, wherein the pattern comprises a series of parallel lines.

3. The method of claim 1, wherein the step of capturing an image of the distorted light pattern comprises processing image data of the captured image of the distorted light pattern.

4. The method of claim 3, wherein the processing of the image data is carried out by the computing system, and the computing system is separate and apart from the combined pattern-casting and imaging device.

5. The method of claim 3, wherein the computing system is part of the combined pattern-casting and imaging device and the combined pattern casting and imaging device is part of a smart device.

6. The method of claim 3, further comprising wirelessly transmitting image data from the combined pattern casting and imaging device to the computing system, over a wireless network.

7. The method of claim 6, wherein the image data is wirelessly transmitted as a live stream video, to the computing system, and the computing system is a remote computing system.

8. The method of claim 1, wherein the combined pattern-casting and imaging device is a cell phone device comprising a flashlight feature, and the step of casting the light pattern against the surface of the skin of the patient comprises:
    fitting an adapter over the flashlight feature to form a pattern projector; and
    casting the light pattern with the pattern projector.

\* \* \* \* \*